United States Patent [19]

Farris et al.

[11] 4,292,039

[45] Sep. 29, 1981

[54] METHOD AND APPARATUS FOR CONTROLLING DISSOLVED SOLID CONCENTRATIONS

[76] Inventors: Clyde A. Farris, 1736 Choto Rd.; Clyde A. Farris, Jr., 11130 Crown Point Dr., both of, Knoxville, Tenn. 37922

[21] Appl. No.: 133,514

[22] Filed: Mar. 24, 1980

[51] Int. Cl.³ .................... G01N 27/00; G01N 27/26
[52] U.S. Cl. .................................. 23/230 A; 422/62
[58] Field of Search ................. 23/230 A; 422/62; 364/499, 500

[56] References Cited

U.S. PATENT DOCUMENTS

| | | | |
|---|---|---|---|
| 3,578,431 | 5/1971 | Ingestad et al. | 422/62 X |
| 3,607,549 | 9/1971 | Bielefeld, Jr. | 422/62 X |
| 4,055,751 | 10/1977 | Bussman et al. | 422/62 X |
| 4,172,880 | 10/1979 | Tzavos | 422/62 X |

Primary Examiner—Ronald Serwin

[57] ABSTRACT

A method and apparatus are provided for controlling the concentrations of dissolved solids in a plurality of solutions contained in a plurality of interconnected baths. The conductivities of the solutions are monitored and make-up liquid is added to each bath when the conductivity of the respective solution exceeds a predetermined level.

7 Claims, 7 Drawing Figures

METHOD AND APPARATUS FOR CONTROLLING DISSOLVED SOLID CONCENTRATIONS

The present invention relates to rinsing systems and more particularly to a system for maintaining optimal concentrations of dissolved solids in a plurality of interconnected rinsing baths.

There are many industrial applications in which products are treated with a solution, e.g. a bleach, a dye, a finish or an acid. After a selected period of time, the treating solution must be removed to avoid damaging the product or before a further manufacturing step can be performed. Typically, the product is sequentially rinsed in a plurality of baths to remove the initial treating solution. The products are frequently rinsed on a continuous basis, in contrast to a batch basis. The rinsing solutions contained in the baths are regularly replenished because otherwise the concentrations of the solutions gradually change until they fail to remove all of the process solution from the products.

Although the systems are generally run on a continuous basis, the conditions of the product and the baths are not static. For example, there are often irregular variations over time in the amount of solution carried into the baths by the products. As a result, the concentrations of the baths vary in an unpredictable fashion. In order to overcome these unpredictable variations, which often lead to defective products, it is common to overcompensate in the replenishment of the baths with fresh rinsing liquid. This overcompensation leads to an obvious waste of rinsing liquid. Moreover, if the liquid is heated or cooled, there is a consequential waste of energy, an undesirable expense.

One example of such a rinsing system is used in the manufacture of certain textile products, in which a continuous web of fabric is bleached with an alkaline solution, such as sodium hydrosulfite and/or other chemical additives. However, the bleaching solution is promptly rinsed from the fabric in order to avoid yellowing or other damage to the fabric.

Similarly, in dye rinsing and finishing operations, the process solutions are promptly removed from the material.

In a typical fabric rinsing system, after the web is treated with a process solution, it is successively immersed in a plurality of interconnected rinsing baths, for example four rinsing baths. The four rinsing baths contain rinsing solutions which are successively diluted, i.e. the first bath is the most concentrated with chemical additives and the fourth bath is the least concentrated with chemical additives, essentially chemical free. This successive dilution is accomplished by adding fresh water to the fourth bath, running a countercurrent flow from the fourth bath to the first bath, and then discharging the water and chemical additive solution from the first bath for waste treatment and/or disposal.

After the fabric has been bleached, dyed or otherwise chemically treated, it is directed into a first rinse bath where an initial portion of the chemicals are rinsed from the fabric solution. A portion of the chemical additives is removed from the fabric to remain in the first bath. The fabric thus exits from the first bath carrying a first diluted solution. Thereafter, the fabric is sequentially immersed in the second, third and fourth baths, each of which removes an additional portion of the chemical additives. As the fabric exits from the fourth bath, it is substantially free of the chemical additives. However, the pH may be unacceptable, either high or low, and require further adjustment.

In some instances, where the solution carried by the product is alkaline, it is then immersed in an appropriate pH bath, for example, acetic acid, to neutralize the slight alkalinity of the solution carried by the web after exit from the fourth bath. In other operations, the product may carry an acidic solution and require alkaline neutralization in a similar manner. This final immersion is intended to ensure that there is no residual alkalinity or acidity in the fabric, other than as desired.

In order for the fabric to emerge from the pH control bath in the desired condition, there is an optimal concentration of chemical and mineral salts for each of the baths and an optimal pH for the pH bath.

If the fabric web were run absolutely continuously at a constant speed through the rinsing baths, if the initial bleaching solution were maintained at a constant concentration, if the web always carried a constant amount of solution per running foot of web, and if the web was always the same width and weight, then the optimal bath concentrations and pH could probably be maintained with merely a constant input of fresh water into bath four and a constant input of pH adjustment chemical and water into the pH bath. However, such ideal conditions do not exist in an operating plant. Instead, the web speed varies, the concentration of the initial chemical solution varies and the amount of solids carried by the fabric varies with the particular weave and the varying character of the yarn. Each of these variations contributes to overall changes in the concentrations of the baths, i.e., deviation from the optimal concentrations. Consequently, constant inputs of fresh water and pH adjustment chemical cannot maintain the optimal concentration. These deviations accumulate and, over time, lead to substantial changes in concentrations and a decline in product quality.

As noted above, heretofore it has been standard practice to merely overcompensate for possible deviations, adding excess fresh water and excess pH adjustment chemical. Manual checks are occasionally made to see whether the final product is too alkaline or too acidic and suitable manual adjustments are made. This procedure does not lead to a uniform product because several variations can occur between testing, and the variations are not detected until it is too late to remedy the situation. The product is already damaged. It is not uncommon for a bleaching dying or finishing plant to have a rejection rate as high as 30%.

In addition to the tremendous losses caused by defective products, the overcompensation of fresh water and pH adjustment chemical is also expensive. The additional costs of overcompensation occur in at least three forms. First, there is the added cost of the wasted materials comprised of water and pH adjustment chemical. Secondly, there are additional fuel expenses because the rinsing baths are generally maintained at elevated temperatures, for example, between about 120° F. and 180° F. Any excess water added to the baths constitutes a waste of the fuel used to heat it as input water is approximately 55° F. prior to heating. Thirdly, all of the solution exiting from the first bath must be treated before it can be disposed. Excess solution requires excess equipment capacity as well as additional treating materials. These excess costs caused by overcompensation are substantial in some operations.

It is therefore an object of the present invention to provide a system for continuously monitoring and maintaining generally constant concentrations of a plurality of interconnected rinsing baths. It is also an object to provide a system for minimizing the waste of materials and fuel in a rinsing system. It is a further object to improve the quality and uniformity of products exiting from a plurality of interconnected rinsing baths.

Further objects and advantages will be apparent when the following description is considered in connection with the drawings in which.

Figure 1:
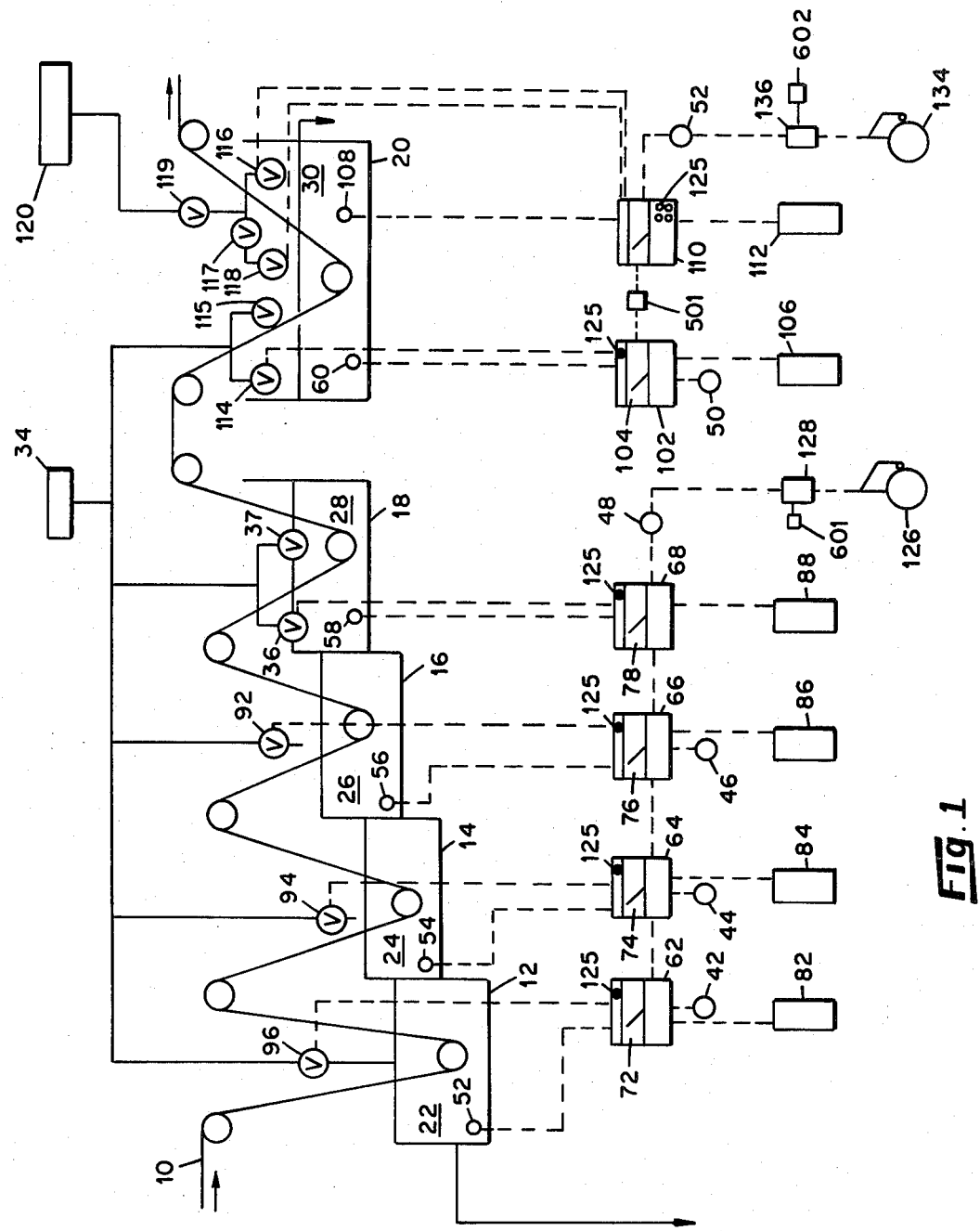
FIG. 1 is a schematic diagram of a system embodying various of the features of the present invention.
Figure 2:
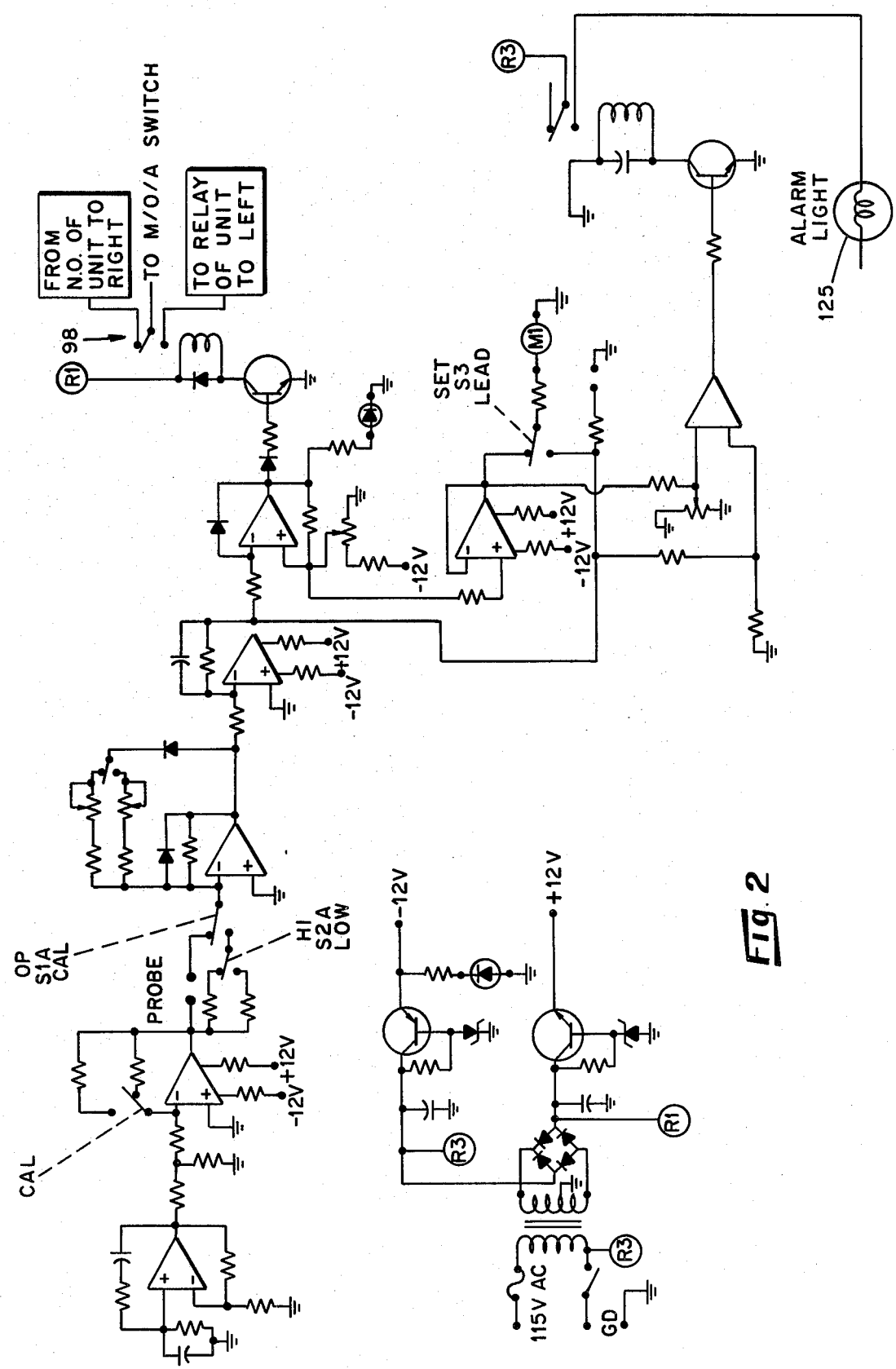
FIG. 2 is a schematic diagram of a controller for the system shown in FIG. 1.
Figure 3:
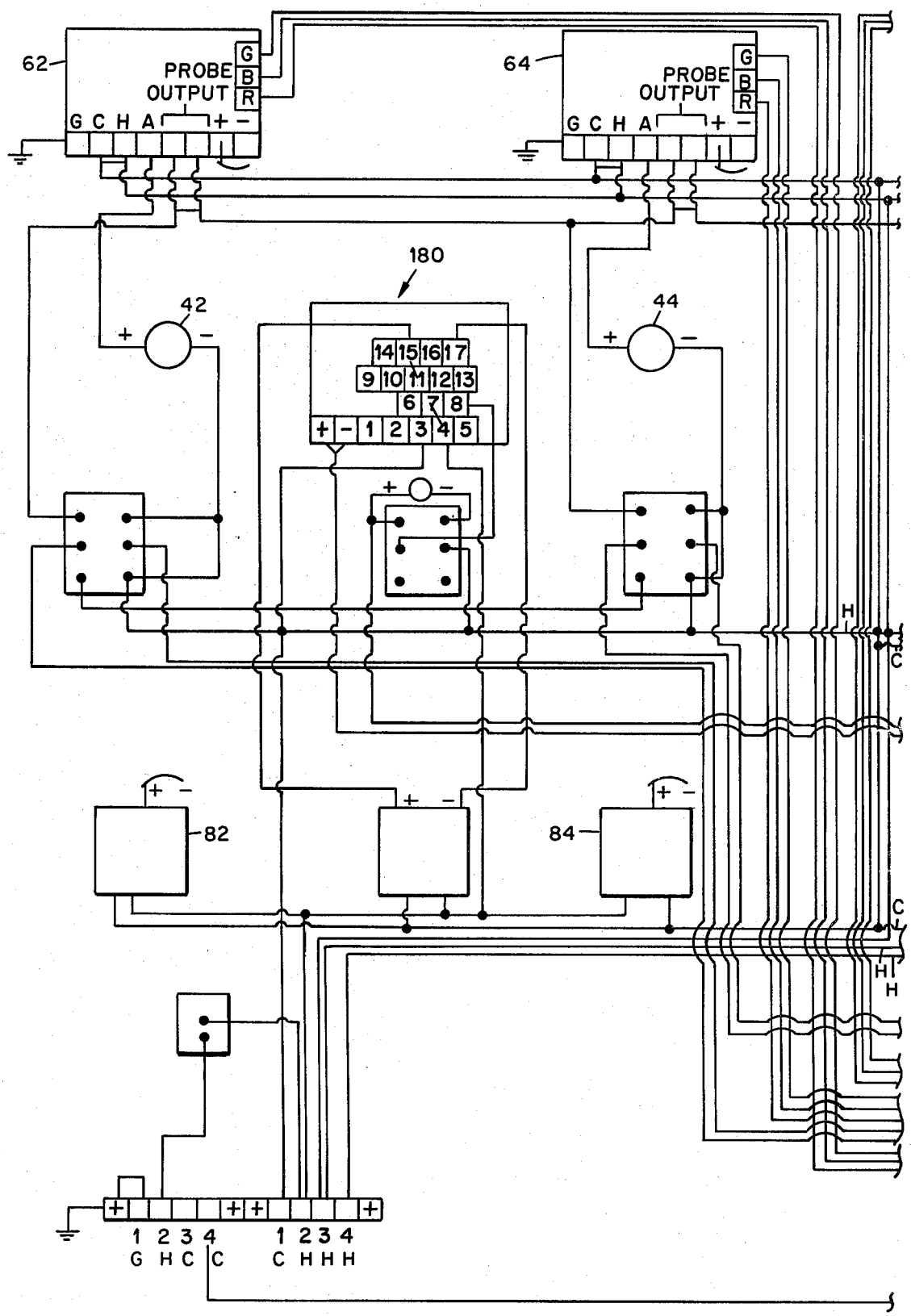
FIG. 3 is a partial diagrammatic view of a system embodying various of the features of the present invention.
Figure 4:
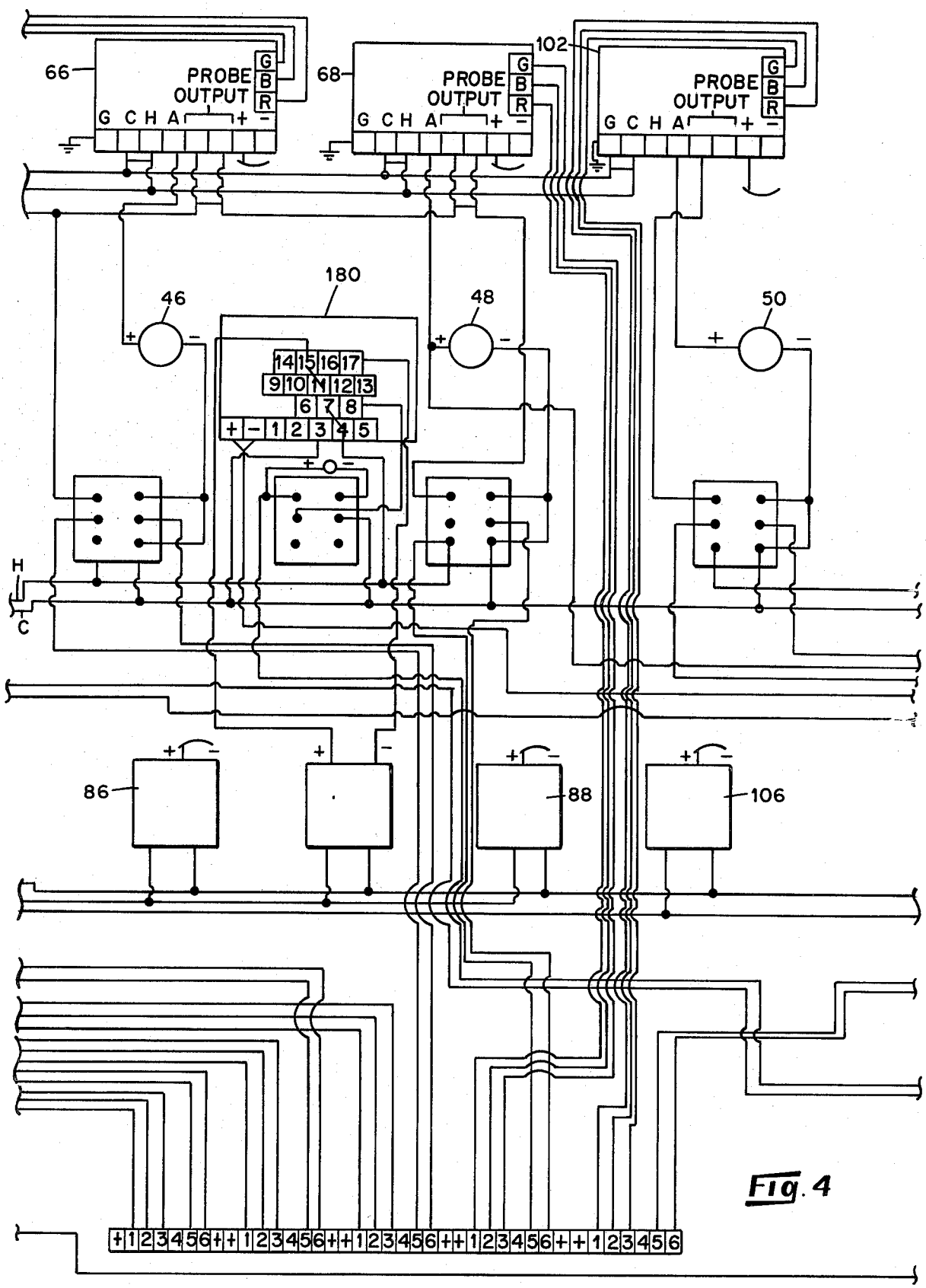
FIG. 4 is a partial diagrammatic view continuing from FIG. 3.
Figure 5:
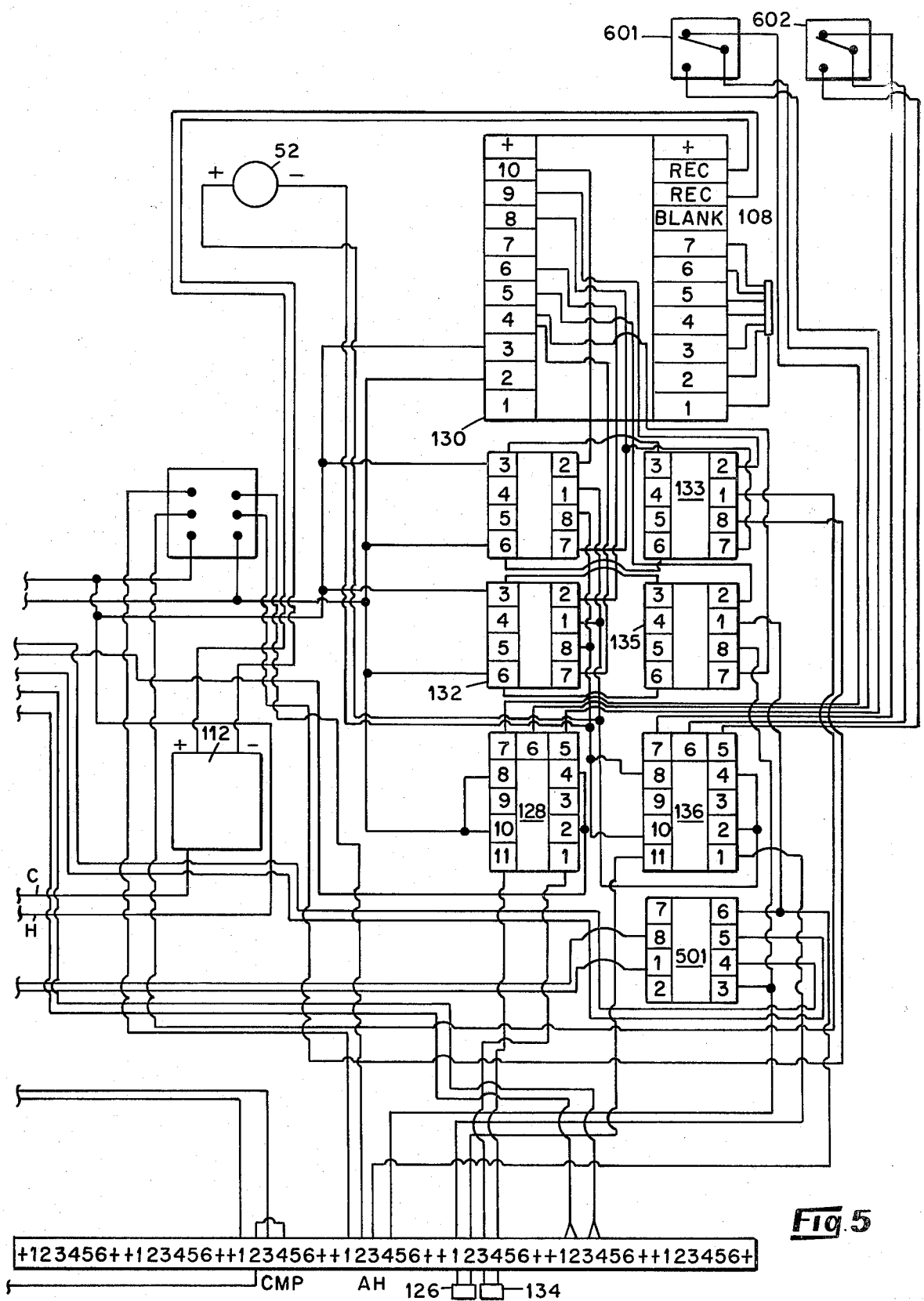
FIG. 5 is a partial diagrammatic view continuing from FIG. 4.
Figure 6:
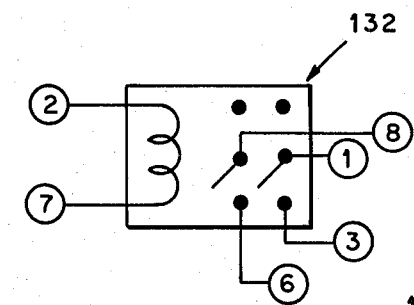
FIG. 6 is a diagrammatic view of a control relay included in the pH analyzer of the system shown in FIG. 1.
Figure 7:
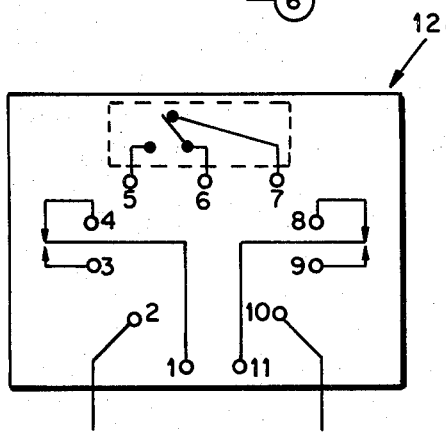
FIG. 7 is a diagrammatic view of a time delay relay included in the system shown in FIG. 1.

The conductivity of a solution of dissolved solids is proportional to the concentration of dissolved solids. That is, an increase in concentration results in a corresponding increase in conductivity. Consequently, if a solution is maintained at a generally constant conductivity, the concentration of dissolved solids also remains generally constant.

In accordance with the present invention, at least two baths, a first bath and a second bath containing a first rinsing solution and a second rinsing solution, respectively, are connected in flow communication with one another, with the first solution flowing into the second bath. The product being rinsed flows counter to the solution flow. The first rinsing solution is diluted with a make-up liquid to a greater degree than the second rinsing solution. First conductivity monitoring means are placed in contact with the first solution contained in the first rinsing bath. The first conductivity monitoring means are operatively connected to a first valve means controlling the flow of make-up liquid from a make-up liquid source into said first bath. Second conductivity monitoring means are placed in contact with the second solution contained in the second rinsing bath. The second conductivity monitoring means are operatively connected to a second valve means controlling the flow of make-up liquid from the make-up liquid source into said second bath. The first conductivity monitoring means and the second conductivity monitoring means are interconnected so that the second conductivity monitoring means is prevented from opening the second valve means to dilute the second rinsing solution with a make-up liquid unless the first valve is simultaneously open to admit make-up liquid from the make-up liquid source into the first bath.

Referring more particularly to the drawings, in the depicted embodiment, a system is provided for rinsing a continuous fabric web 10 to remove an initial bleaching solution. The system includes four successive alkaline rinsing baths 12, 14, 16 and 18 and a neutralizing acid bath 20. Each of the baths 12, 14, 16, 18, and 20 contains a rinsing solution 22, 24, 26, 28 and 30, respectively. A plurality of conventional directing rollers 32 are located adjacent to and within each of the baths 12, 14, 16, 18, and 20 to direct the fabric web 10 over a path of successive immersion in the baths 12, 14, 16, 18 and 20, prior to drying and rolling for storage or further processing.

The baths 12, 14, 16 and 18 are sequentially interconnected to provide flow communication between successive baths. In the depicted embodiment, flow communication is provided by means of overflow discharge from the bath 18 to the bath 16, from the bath 16 to the bath 14, and from the bath 14 to the bath 12. Make-up liquid is continuously added to the bath 18 from a fresh water source 34 through the valve 37 at a predetermined rate. The rate of flow through the valve 37 is set to maintain a minimum solution overflow from tank 12. Thus, when the baths are full, and water is added to the bath 18, there is an overflow discharge of solution 28 into the bath 16, of solution 26 into the bath 14, and of solution 24 into the bath 12. In addition, there is a final overflow discharge of the solution 22 from the bath 12. The overflow discharge from each of the baths 10, 12, 14, and 16 ensures that there is a maximum volume of rinsing solution in each of the rinsing baths.

The bath 20 is not interconnected with the baths 12, 14, 16 or 18. Instead, a constant input of dilute acid is provided and an overflow discharge maintains a constant volume of solution 30 in the bath 20.

Each of the baths 12, 14, 16, 18 and 20 is provided with conductivity monitoring means, each of which includes an electrode sensor 52, 54, 56, 58 and 60, respectively. Each electrode sensor comprises a 1 volt alternating current, carbon-tipped, temperature-compensated electrode.

The electrode sensor 52 is in constant contact with the solution 22 in the bath 12. The sensor 52 is electrically connected to a controller 62 which includes a meter 72 and an optional recorder 82 adapted for continuous display and recording of the conductivity of the solution 12. As noted above, the conductivity of the solution 22 is proportional to the concentration of dissolved solids. Thus, the recorder 82 provides a continuous record of the mineral salts concentration of the first solution 22. Similarly, each of the baths 14, 16 and 18 is provided with a sensor 54, 56 and 58, respectively, and each of the sensors 54, 56 and 58 is electrically connected to a controller 64, 66 and 68 respectively. Each of the controllers 64, 66 and 68 includes a meter 74, 76 and 78, respectively, and includes an optional recorder 82, 84 and 86, respectively. Thus, there is provided a continuous record of the conductivity, and thus dissolved solids or mineral salts concentrations, of all of the solutions 22, 24, 26 and 28.

The controller 68, which monitors the solution 28 is electrically connected to the solenoid valve 36 which controls the flow of fresh make-up water from the water source 34 to the bath 18. Whenever the conductivity of the solution 28 exceeds a predetermined control point for the solution 28, the controller 68 opens the solenoid valve 36 to add additional fresh water to the solution 28, thus reducing the concentration and conductivity of the solution 28 to a level which yields an acceptable final product.

The controller 66 is electrically connected to a solenoid valve 92 which controls the flow of the fresh water from the source 34 to the bath 16. When the conductivity of the solution 26 exceeds a predetermined control point for the solution 26, the solenoid valve 92 is opened to add fresh water to the bath 14.

Similarly, the controller 64 is electrically connected to a solenoid valve 94 which controls the flow of fresh water from the source 34 to the bath 14. When the conductivity of the solution 24 exceeds a predetermined control point for the solution 24, the solenoid valve 94 is opened to add fresh water to the bath 14.

Also, the controller 62 is electrically connected to a solenoid valve 96 which controls the flow of fresh water from the source 34 to the bath 12. When the conductivity of the solution 22 exceeds a predetermined control point for the solution 22, the solenoid valve 96 is opened to add fresh water to the bath 12.

The solenoid valves 36, 92, 94 and 96 are electrically interconnected with one another by means of a double-pole-double-throw relay 98, built into each of the controllers 62, 64 and 66 such that the valve 92 cannot be opened unless the valve 36 is open, the valve 94 cannot be opened unless the valves 36 and 92 are open and the valve 96 cannot be opened unless the valves 36, 92 and 94 are open. In this manner, fresh water is not added to any "downstream" bath as long as the "upstream" solutions are below the predetermined conductivity control points for those solutions. As a result, there is a large reduction in the amounts of water and fuel used in the process.

The conductivity sensing means 50 for the acid bath 20 includes an electrode sensor 60 like the sensors 52, 54, 56 and 58. The sensor 60 is electrically connected to a controller 102 which includes a meter 104 and an optional recorder 106 adapted for continuous display of the conductivity of the solution 30. The conductivity of the solution 30 is proportional to the concentration of the dissolved solids, in this case the bleaching solution, and the acid concentration. Thus, the recorder 106 provides a continuous record of the total concentration of mineral salts in the solution 30.

The controller 102 is electrically connected to a normally closed solenoid valve 114 which controls flow communication from the fresh water source 34 into the bath 20. When the conductivity of the solution 30 exceeds a predetermined maximum control level, the solenoid valve 114 is opened to add fresh water to the bath 20. As noted above, overflow discharge means are provided in the bath 20 to maintain a constant volume of solution 30 in the bath 20.

Means are also provided for sensing and controlling the pH of the solution 30. The pH sensing means includes a pH probe 108, such as Model P60L-3-1 available from Great Lakes Instrument Co. of Milwaukee, Wis., and a pH analyzer 110, such as Model A70-0-1-0-8, also available from the Great Lakes Instrument Co. of Milwaukee, Wis. The probe 108 is in continuous contact with the solution 30 and electrically connected to the analyzer 110. The analyzer 110 is electrically connected to an optional recorder 112 adapted for providing a continuous record of the pH of the solution 30. The analyzer 110 provides a signal when the pH of the solution 30 exceeds a predetermined maximum level or falls below a predetermined minimum level.

The pH analyzer 110 is also electrically connected to a normally open acid solenoid valve 116 and to a normally closed acid solenoid valve 118. The valve 116 controls flow communication from an acetic acid source 120 into the acid bath 20. In its normally open position, the valve 116 permits an acid flow which is predetermined to provide optimum results under steady state conditions. That is, the amount of acid added to the bath 20 on a constant basis through the valve 116 is exactly the amount theoretically expected to continuously neutralize the web 10. However, as discussed hereinabove, the constant flow of acid does not compensate for the irregularities of an operating system.

The valve 118 controls flow communication from the acetic acid source 120 to the bath 20. When the pH of the solution 30 rises above a predetermined maximum level, the valve 118 is opened to add additional acid to the bath 20 to lower the pH of the solution 30.

When the pH of the solution 30 drops below a predetermined minimum level, the normally opened valve 116 is closed to stop the regular flow of acid to the bath 20 and the normally closed valve 114 is opened to add fresh water to the bath 20, thus raising the pH of the solution 30 above the predetermined minimum level. When the predetermined minimum level is reached, the valve 116 is again opened and the valve 114 is closed.

In operation, the controllers 62, 64, 66, 68 and 102, which are commercially available from the Farris Chemical Company, Inc., of Knoxville, Tenn., under the product designation Water Mizer, continuously monitor the conductivity of the solutions 22, 24, 26, 28 and 30, respectively, and the analyzer 110 continuously monitors the pH of the solution 30. The conductivities of the solutions 22, 24, 26, 28, and 30 and the pH of the solution 30 are continuously recorded by the optional recorders 82, 84, 86, 88, 106 and 112, respectively.

When the conductivity of the solution 28 exceeds the control point for that solution, for example 280 micromhos, the controller 68 sends a signal to open the valve 36 to dilute the solution 28 with additional fresh water and reduce the conductivity thereof. The controller 68 simultaneously sends a signal to the relay 98 of the controller 66 to indicate that the valve 36 is open. When the conductivity of the solution 28 falls below the control point, the controller 68 causes the valve 36 to return to its normally closed position and halts the signal to the relay 98 of the controller 66.

When the conductivity of the solution 26 exceeds the control point for that solution, for example 700 micromhos, the controller 66 sends a signal to the relay 98 of the controller 66. If the relay 98 of the controller 66 simultaneously receives a signal from the controller 68, indicating that the valve 36 is open, and a signal from the controller 66 indicating that the solution 26 requires dilution, the relay 98 of the controller 66 is activated to open the valve 92 and simultaneously send a signal to the relay 98 of the controller 64. The valve 92 is opened to add fresh water to dilute the solution 26 and reduce the conductivity thereof until the conductivity falls below the control point for the solution 26 and the valve 92 is returned to its normally closed position.

When the conductivity of the solution 24 exceeds the control for that solution, for example 2450 micromhos, the controller 64 sends a signal to the relay 98 of the controller 64. If the relay 98 of the controller 64 simultaneously receives a signal from the relay 98, of the controller 66, indicating that the valves 36 and 92 are open, and a signal from the controller 64, indicating that the solution 24 requires dilution, the relay 98 of the controller 64 is activated to open the valve 94 and simultaneously send a signal to the relay 98 of the controller 62. The valve 94 is opened to add fresh water to the bath 14, diluting the solution 24 and reducing the conductivity thereof until the conductivity of the solution 24 is reduced below the control point for the solution 24. Then the valve 94 is returned to its normally closed position.

When the conductivity of the solution 22 exceeds the control point for that solution, for example 5000 micromhos, the controller 62 sends a signal the relay 98 of the controller 62. If the relay 98 of the controller 62 simultaneously receives a signal from the relay 98 of the controller 64, indicating that the valves 36, 92 and 94 are open, and a signal from the controller 62, indicating that the solution 22 requires dilution, the relay 98 of the controller 62 is activated to open the valve 96. The valve 96 is opened to add fresh water to the bath 12, diluting the solution 22, until the conductivity of the solution 22 is reduced to a level below the control point for that solution. Then the valve 96 is returned to its normally closed position.

Each of the controllers 62, 64, 66 and 68 includes a control light 125 which is activated whenever the control point for the respective solution is met or exceeded. In addition, each of the controllers 62, 64, 66, 68 and 102 includes an alarm lights 42, 44, 46, 48, and 50 respectively. The alarm circuitry is designed such that, at a given conductivity level, for example 100 micromhos, above the respective control point, a 2 inch diameter alarm light is illuminated to advise the operator that the respective solution is above desired control by the predetermined level. The alarm function operates on each controller 62, 64, 66, 68, and 102 independant of the relays 98 or of the operation of the solenoid valves. For example, if controller 66 goes into an alarm condition because of a sudden surge in the conductivity of the solution 26, the alarm light 46 is activated. Nevertheless, the valve 92 is opened only if the controller 68 has signaled relay 98 and opened valve 36 as outlined above.

In the above-described manner, substantial cost savings are achieved because it is not necessary to dilute the solutions 26, 24 or 22 as long as the upstream solutions have satisfactory concentrations of dissolved solids. The upstream solutions, particularly the solution 28, are better indicators of the quality of the web 10, the truly important consideration.

Under most conditions, the automatic operation of the valves 36, 92, 94, and 96, is sufficient to overcome the intermittent, small changes in the concentrations of the solutions 22, 24, 26, and 28. That is, irregularities in the concentrations are usually corrected within a short period of time without any intervention by an operator.

However, there are times when it becomes necessary for an operator to intervene in the operation, such as if there is a large, sudden change in the bleaching solution. In order to compensate for large changes in the bleach concentrations, the controller 68 is electrically connected through the alarm light 48 and through a time delay relay 128 to an alarm bell 126. When the conductivity of the solution 28 exceeds the control point of the solution 28 by a predetermined amount, such as 100 micromhos, for example, the alarm light 48 is activated in turn activating the alarm bell 126 to notify an operator that a large concentration change in the solution 28 has occurred. At this point the operator manually increases the addition of fresh water to the bath 18 through valve 37. In addition, the operator may activate the time delay relay 128 by switch 601 to permit automatic adjustment to proceed with the increased flow through valve 37 for a predetermined period, three minutes for example. After the adjustment period, the alarm bell 126 is reactivated by the relay 128 if the conductivity of the solution has not been reduced satisfactorily in the intervening period.

At the same time that the solutions 22, 24, 26 and 28 are controlled as to conductivity, the acidic solution 30 is simultaneously controlled for both conductivity and pH. When the conductivity of the solution 30 exceeds the control point of the solution 30, for example, 400 micromhos, the controller 102 opens the valve 114 to add fresh water to the bath 20, thus diluting the solution 30. When the conductivity falls below the control point, the valve 114 is closed again. If the conductivity of the solution 30 exceeds the control point by a predetermined amount, such as 100 micromhos, the alarm light is activated to notify the operator that the flow through valve 115 should be increased.

The analyzer 110 is a four control point unit, i.e. low-low, low, high and high-high. The pH of the solution 30, is maintained within a tight pH range to insure that the web 10, after leaving the solution 30, will be acidic, yet after air contact and drying will have a neutral pH of 7.0. If the dried product has either a higher or a lower pH than neutral, the product is unacceptable because degradation of the product fibers occurs. In a dye rinse operation, colors fade or streaking or spotting occurs if the pH is not closely controlled.

The pH of the solution 30 is controlled between a predetermined control range, for example, 4.5 to 5.0 pH.

The analyzer 110 provides a direct readout of pH and allows acid to flow from the source 120 through the normally open valve 116. If the pH of the solution 30 drops to a predetermined low point, e.g., 4.5 pH, the low control point relay 135 closes valve 116 to stop acid flow and overrides the controller 102, through relay 501, to open valve 114. In this manner, the pH of the solution 30 is raised because the supply water from the source 34 is of significantly higher pH than the desired pH in the solution 30. If the pH of solution 30 falls below the low control point by 0.3 pH unit, for example, a so-called low-low control point, the analyzer 110 activates the low-low control relay 132 which activates the alarm light 52 and, through the relay 136, activates alarm bell 134. Only the alarm bell is deactivated by switch 602 through the time delay relay 136. The alarm light 52 is not deactivated by the switch 602. The operator may take necessary steps to manually adjust the pH or wait for a predetermined time, three minutes for example, for automatic adjustment. The alarm bell 134 is reactivated by relay 136 if the pH of the solution 30 has not increased satisfactorily in the intervening period. Should the pH rise to the high control point, for example 5.0 pH, the high control relay 133 opens the normally closed solenoid valve 116 to allow additional acid to be added to the solution 30. Should the pH of solution 30 increase above the high control by a predetermined amount, for example, 0.3 pH units, to pH 5.3, a so-called high-high control point, the analyzer 110 activates alarm bell 134. Only the alarm bell can be deactivated by switch 602 through the time delay relay 136. The alarm light 52 is not deactivated by the switch 602. The operator must take necessary steps including increasing the flow through valve 119, a globe valve. The operator can then wait for the remainder of the predetermined time, for example, 3 minutes, for automatic adjustment of this high-high pH condition. After the adjustment period, the alarm bell 134 is reactivated if the pH of solution 30 has not decreased satisfactorily in the intervening period.

In dye and finishing operations, the dyes most often used are acid dyes, in contrast to the alkaline solutions of a bleaching operation. Therefore, the pH analyzer 110 controls the pH by increasing the pH of the solution 30 rather than lowering the pH. To this end, an alkaline solution is fed through valves 116 and 118 to give the final product a neutral or other desired pH to eliminate color fade, spotting, streaking or acid attach on the product.

In some operations, temperature is an important factor, in the quality of the finished product, whether it be in finishing, dyeing or bleach rinsing operations. Control of temperature is directly related to the effective removal of solids, (bleaching compound, dyes, mineral salts, etc.) from the product. Heat exchangers and live steam injection are used to raise the temperature of fresh water, from a mean input temperature of about 50° F. to the desired control temperature of 120° F. to 180° F., for example. Manual adjustment by operators by use of manual thermometers allows wide fluctuations of temperatures by as much as 45° F. and often temperatures above 210° F. will be found in a typical manual operation. Naturally when this fluctuation occurs, the resulting energy waste of boiler fuel, oil and gas is exceedingly large. In addition, poorer rinsing characteristics are provided. In the depicted embodiment, temperature controllers 180, including thermocouples, control temperatures within 3° F. Alternatively, direct readout temperature units are used with thermocouples if manual control of temperature is desired. Where desirable, temperature recorders may be included. When temperatures are controlled in connection with the practice of the present invention, better rinsing is maintained at a given temperature, with less water waste and fewer solids are carried over from bath to bath.

Employing a system as described herein, the resulting textile product is substantially constant in quality and the rejects are reduced to a very low level. Moreover the usage of water, chemical additives and energy were reduced to great degree.

While a preferred embodiment of the method and apparatus of the present invention has been illustrated and described herein, it will be understood that changes and modifications may be made therein without departing from the invention in its broader aspects. The description is intended to limit the invention only as set forth in the claims attached hereto.

I claim:

1. A system for maintaining generally constant concentrations of solutions contained in a plurality of sequentially communicating liquid baths for treating a fabric web by successive immersion in said liquid baths including a first bath containing a first solution having a first concentration of dissolved solids and a second bath containing a second solution having a second concentration of dissolved solids, said first solution flowing from said first bath into said second bath said system comprising first conductivity monitoring means in contact with said first solution and operatively connected to a first valve means controlling flow communication from a source of make-up liquid into said first bath, second conductivity monitoring means in contact with said second solution and operatively connected to a second valve means controlling flow communication from said source of make-up liquid into said second bath, and means for interlocking said first conductivity monitoring means to said second conductivity monitoring means, whereby said second conductivity monitoring means is inoperative with respect to said second valve means unless said first valve means is open to admit make-up liquid from said source to said first bath.

2. A system as defined in claim 1 wherein said interlocking means comprises a relay electrically connected to said first monitoring means and said second conductivity monitoring means.

3. A system as defined in claim 1 and further comprising a neutralizing bath containing a neutralizing solution, conductivity monitoring means in contact with said neutralizing solution and operatively connected to valve means controlling flow communication from a source of make-up liquid for said neutralizing solution to said neutralizing bath.

4. A system as defined in claim 1 wherein said second concentration is greater than said first concentration.

5. A method for maintaining generally constant concentrations of solutions contained in a plurality of sequentially communicating liquid baths for treating a fabric web by successive immersion in said liquid baths, including a first bath containing a first solution having a first concentration of dissolved solids and a second bath containing a second solution having a second concentration of dissolved solids, comprising
monitoring the conductivity of said first solution,
adding make-up liquid to said first solution when the conductivity of said first solution exceeds a predetermined control point for said first solution,
flowing said first solution into said second bath,
monitoring the conductivity of said second solution,
adding make-up liquid to said second solution when the conductivity of said second solution exceeds a predetermined control point for said second solution, and
preventing the addition of make-up liquid to said second solution unless the conductivity of said first solution exceeds the predetermined control point for said first solution.

6. A method as defined in claim 5 wherein said control point for said second solution is greater than the control point for said first solution.

7. A method as defined in claim 5 and further comprising maintaining said first solution at a predetermined temperature and maintaining said second solution at a predetermined temperature.

* * * * *